US005543536A

United States Patent [19]

Tam

[11] Patent Number: 5,543,536
[45] Date of Patent: Aug. 6, 1996

[54] MONODENTATE PHOSPHITE AND NICKEL CATALYST COMPOSITION FOR MONOOLEFIN HYDROCYANATION

[75] Inventor: Wilson Tam, Boothwyn, Pa.

[73] Assignee: E. I. Du Pont de Nemours and Company, Wilmington, Del.

[21] Appl. No.: 233,194

[22] Filed: Apr. 26, 1994

[51] Int. Cl.$^6$ .............................. C07F 9/02; C07F 15/04
[52] U.S. Cl. ................ 556/13; 556/138; 502/162; 558/338; 568/14
[58] Field of Search ............ 556/13, 138; 558/338; 568/14; 502/162

[56] References Cited

U.S. PATENT DOCUMENTS

| | | | |
|---|---|---|---|
| 3,496,210 | 2/1970 | Drinkard, Jr. et al. | 260/465 |
| 3,496,217 | 2/1970 | Drinkard, Jr. et al. | 260/465.8 |
| 3,631,191 | 12/1971 | Kane et al. | 260/439 R |
| 3,655,723 | 4/1972 | Drinkard, Jr. | 260/465.3 |
| 3,766,237 | 10/1973 | Chia et al. | 260/465.3 |
| 4,599,206 | 7/1986 | Billig et al. | 558/85 |
| 4,717,775 | 1/1988 | Billig et al. | 568/454 |
| 4,774,353 | 9/1988 | Hall et al. | 558/335 |
| 4,874,884 | 10/1989 | McKinney | 558/338 |

FOREIGN PATENT DOCUMENTS

| | | |
|---|---|---|
| 1417554 | 12/1975 | United Kingdom . |
| WO93/03839 | 3/1993 | WIPO . |

OTHER PUBLICATIONS

Baker, M. J. et al, *J. Chem. Soc. Chem. Comm.*, 1292–1293, 1991.
Baker, M. J. et al, *J. Chem. Soc. Commun.*, 803–804, 1991.
Cuny, G. D. et al, *J. Am. Chem. Soc.*, 115, 2066–2068, 1993.
Tolman, C. A. et al, *Advances in Catalysis*, 33, 2–46, 1985.
Tam, Wilson, et al., "Process and Catalyst Composition for Hydrocyanation of Monoolefins", CR–9432–A, U.S. Ser. No. 08/198,963, filed Feb. 18, 1994.
Kreutzer, Kristina A., et al., "Bidentate Phosphite and Nickel Composition for Hydrocyanation of Monoolefins", CR–9507, U.S. Ser. No. 08/227,802, filed Apr. 14, 1994.

*Primary Examiner*—Porfirio Nazario-Gonzales

[57] ABSTRACT

Catalyst compositions comprising zero-valent nickel and a mondentate phosphite ligand are provided, with a process for the hydrocyanation of monoolefins using these compositions in the presence of a Lewis acid promoter.

18 Claims, No Drawings

MONODENTATE PHOSPHITE AND NICKEL CATALYST COMPOSITION FOR MONOOLEFIN HYDROCYANATION

This invention relates to the hydrocyanation of monoolefins in the presence of zero-valent nickel, a monodentate phosphite ligand and a Lewis acid promoter.

Hydrocyanation catalyst systems, particularly pertaining to the hydrocyanation of olefins, are well known in the art. For example, catalyst systems useful for the hydrocyanation of butadiene to form pentenenitrile (PN) and in the subsequent hydrocyanation of PN to form adiponitrile (ADN), are widely used in commercial nylon synthesis. The hydrocyanation of activated olefins such as conjugated olefins, e.g., butadiene and styrene, and strained olefins, e.g., norbornene, proceeds without the use of a Lewis acid promoter, while hydrocyanation of unactivated olefins such as 1-octene and 3 PN requires the use of a Lewis acid promoter. Use of promoters in the hydrocyanation reaction is described in, for example, U.S. Pat. No. 3,496,217. This patent discloses an improvement in hydrocyanation using a promoter selected from a large number of metal cation compounds with a variety of anions as catalyst promoters. U.S. Pat. No. 3,496,218 discloses a nickel hydrocyanation catalyst promoted with various boron-containing compounds, including triphenylboron and alkali metal borohydrides. U.S. Pat. No. 4,774,353 discloses a process for preparing dinitriles, including ADN, from unsaturated nitriles, including pentenenitriles, in the presence of a zerovalent nickel catalyst and a triorganotin catalyst promoter. U.S. Pat. No. 4,874,884 dislcoses a process for producing ADN by the zerovalent nickel-catalyzed hydrocyanation of pentenenitriles in the presence of a synergistic combination of promoters selected in accordance with the reaction kinetics of the ADN synthesis.

Bidentate phosphite ligands are known to be useful ligands in the zerovalent nickel-catalyzed and rhodium-catalyzed hydrocyanation of activated olefins. See, for example: Baker, M. J. and Pringle, P. G.; J. Chem. Soc., Chem. Commun., 1292 (1991); Baker, M. J.; Harrison, K. N.; Orpen, A. G.; Pringle, P. G.; and Shaw, G.; J. Chem. Soc.; Chem. Commun., 803 (1991); WO 93/03839 (Union Carbide); and Cuny, D. G. and Buchwald, S. L., J. Am. Chem. Soc. (1993) 115, 2066–2068. Hydrocyanation of unactivated olefins catalyzed by select bidentate phosphite ligands and zerovalent nickel in the presence of Lewis acid promoters is disclosed in commonly assigned application U.S. Ser. No. 08/198,963.

The hydrocyanation of olefins catalyzed by transition metal complexes with monodentate phosphite ligands is disclosed in the prior art. See, for example: U.S. Pat. Nos. 3,496,210, 3,631,191, 3,655,723 and 3,766,237, and Tolman, C. A., McKinney, R. J., Seidel, W. C., Druliner, J. D., and Stevens, W. R., Advances in Catalysis, 33, 1 (1985). Monodentate ligands similar to those employed in the present invention for the hydrocyanation of monoolefins are disclosed in WO 93/03839, and are said to be useful in the asymmetic hydrocyanation of prochiral olefinic compounds in the presence of an optically active zerovalent nickel-ligand complex catalyst. Mondentate ligands are also known with nickel carbonyl complexes in the hydrocyanation of olefins; Great Britian 1,417,554.

SUMMARY OF THE INVENTION

The present invention provides a process for hydrocyanation comprising reacting a nonconjugated acylic aliphatic monoolefin or a monoolefin conjugated to an ester group, e.g., methyl pent-2-eneoate, with a source of HCN in the presence of a catalyst precursor composition comprising zero-valent nickel and a monodentate phosphite ligand of Formula I,

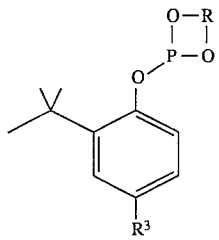

wherein:

R is

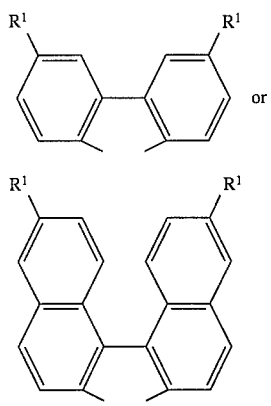

each $R^1$, independently, is H, $C_{1-8}$ alkyl or $OR^2$;

$R^2$, independently, is $C_{1-8}$ alkyl; and $R^3$, is H, $C_{1-8}$ alkyl or $OR^2$;

and wherein said reaction is carried out in the presence of a Lewis acid promoter, to produce a terminal organonitrile.

The olefins used in the invention process are of the formula $$CH_3—(CH_2)_y—CH=CH—(CH_2)_x—R^4 \qquad (II)$$

or $$CH_2=CH—(CH_2)_x—R^4 \qquad (III)$$

wherein:

$R^4$ is H, CN, $CO_2R^5$ or $C_z(F_{2z+1})$;

x is 0 or 1–5;

y is 0 or 1–5;

$R^5$ is $C_{1-8}$ alkyl; and z is 1–8.

with the proviso that when $R^4$ is CN, x is not zero.

It is believed that the present invention will be operable with alkyl groups in $R^1$, $R^2$, $R^3$ and $R^5$ containing up to at least 12 carbon atoms, and with x and y up to at least 8.

The present invention further provides a catalyst precursor composition comprising zero-valent nickel or precursor thereto and a monodentate phosphite ligand of Formula I described hereinabove, said ligand and nickel source being present in an amount such that the g atom ratio P:Ni is in the range of about 1:1 to 10:1.

DETAILED DESCRIPTION OF THE INVENTION

The products of the hydrocyanation process of the present invention wherein the starting olefin is of Formula II or Formula III are represented, respectively, by Formulas IV and V:

$$NC—(CH_2)_{x+y+3}—R^4 \qquad \text{IV}$$

$$NC—(CH_2)_{x+2}—R^4 \qquad \text{V}$$

wherein the symbols have the same meaning as above.

The catalyst precursor composition of the invention is comprised of a monodentate phosphite ligand and zero-valent nickel or precursor thereto. The amounts of ligand and nickel source present are such that the g atom ratio P:Ni is in the range of about 1:1 to 10:1. The phosphite ligand is of Formula I

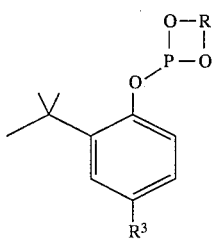

wherein R is

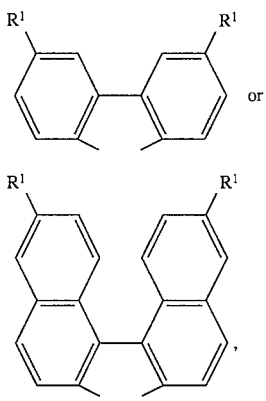

each $R^1$, independently, being H, $C_{1-8}$ alkyl which may be linear or branched, or $OR^2$ wherein $R^2$ is $C_{1-8}$ alkyl. $R^2$ may also be linear or branched; examples include methyl, ethyl, isopropyl and t-butyl. Each $R^3$ is H, $C_{1-8}$ alkyl which may be linear or branched, or $OR^2$ where $R^2$ is defined as above.

In the preferred ligand, R is 1,1'-biphenyl; $R^1$ is H; and $R^3$ is $OR^2$ where $R^2$ is methyl.

By "catalyst precursor composition" is meant the mix of catalyst ingredients entering the hydrocyanation reaction. It is believed that the active catalyst during hydrocyanation may be complexed to an olefin.

The ligand of Formula I may be prepared by methods known in the art. Suitable preparative methods are described in, for example, WO 93,03839, which is hereby incorporated by reference. The reaction of 2,2'-biphenol or 2,2'-binaphthol with phosphorus trichloride gives 1,1'-biphenyl- (or 1,1'-binaphthyl) 2,2'-diyl phosphorochloridite. Reaction of the phosphochloridite with 2-t-butyl-4-methoxyphenol in the presence of triethylamine gives the preferred ligand wherein $R^3$ is methoxyl.

The zero-valent nickel can be prepared or generated according to methods well known in the art (U.S. Pat. Nos. 3,496,217; 3,631,191; 3,846,461; 3,847,959; and 3,903,120 which are hereby incorporated by reference). Zero-valent nickel compounds containing ligands which can be displaced by the organophosphorus ligand of Formula I are a preferred source of zero-valent nickel. Such preferred zero-valent nickel compounds include $Ni(COD)_2$ (COD is 1,5-cyclooctadiene) and $Ni(P[O-o-C_6H_4CH_3]_3)_2(C_2H_4)$, both of which are known in the art. Alternatively, divalent nickel compounds combined with a reducing agent provide a suitable source of zero-valent nickel in the hydrocyanation reaction. Suitable divalent nickel compounds include those of the formula $NiY_2$ where Y is halide, carboxylate, or acetylacetonate. Suitable reducing agents include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120, is also a suitable source of zero-valent nickel.

The nonconjugated acyclic aliphatic monoolefin substrates of the invention are represented by Formulas II and III $$CH_3\ (CH_2)_y—CH=CH(CH_2)_x—R^4 \qquad \text{(II)}$$

$$CH_2=CH(CH_2)_x—R^4 \qquad \text{(III)}$$

wherein:

$R^4$ is H, CN, $CO_2R^5$ or $C_z(F_{2z+1})$;

x is 0 or 1–5;

y is 0 or 1–5;

$R^5$ is $C_{1-8}$ alkyl; and z is 1 to 8.

with the proviso that when $R^4$ is CN, x is not 0.

Suitable monoolefin substrates include unsaturated organic compounds containing up to about 18 carbon atoms and having at least one nonconjugated aliphatic carbon—carbon double bond. Suitable unsaturated compounds include nonsubstituted olefins and olefins substituted with groups which are chemically inert towards the catalyst, such as cyano. These unsaturated compounds include monoolefins containing up to about 18 carbon atoms, such as ethylene, propylene, 1-butene, 2-pentene, 2-hexene and the like; nonconjugated diolefins such as allene; and substituted compounds such as 3-pentenenitrile, 4-pentenenitrile and methyl pent-3-enoate. The monoolefins may also be conjugated to an ester group such as methyl pent-2-enoate.

Preferred substrates are nonconjugated linear alkenes, nonconjugated linear alkenenitriles, nonconjugated linear alkenoates, linear alk-2-enoates and perfluoroalkyl ethylenes. Most preferred substrates include 3- and 4-pentenenitriles, alkyl 2- and 3- and 4-penteneoates, and $C_zF_{2z+1}CH=CH_2$, where z is 1 to 8. 3-pentenenitrile is especially preferred.

Substrates of Formula II and Formula III yield terminal nitriles of Formula IV and Formula V, respectively:

$$NC—(CH_2)_{x+y+3}—R^4 \qquad \text{IV}$$

$$NC—(CH_2)_{x+2}—R^4 \qquad \text{V}$$

wherein the symbols have the same meaning as above.

The preferred products are terminal linear alkanenitriles, linear alkanedinitriles, linear alkanenitrile esters, and 3-(perfluoroalkyl)propionitrile. More preferred products are adiponitrile, alkyl 5-cyanovalerate, and $C_zF_{2z+1}CH_2CH_2CN$ where z is 1 to 8. Most preferred is adiponitrile.

The present hydrocyanation process may be carried out by slowly charging a reactor with all of the reactants, or preferably, by slowly charging the reactor with the catalyst precursor or catalyst components, the unsaturated organic compound, the Lewis acid promoter, a suitable solvent, and hydrogen cyanide (HCN). HCN may be delivered to the reactor as a liquid or as a vapor. Alternatively, the reactor may first be charged with the catalyst, promoter, and solvent, and then slowly fed with the unsaturated organic compound and HCN. The molar ratio of unsaturated organic compound to catalyst precursor components is generally in the range of about 10:1 to about 2000:1.

Preferably, the hydrocyanation reaction medium is agitated, such as by stirring or shaking. The cyanated product can be recovered by conventional methods such as distillation. The reaction may be carried out either batchwise or continuously.

The hydrocyanation reaction may be carried out with or without a solvent. Optional solvent should be a liquid under reaction conditions and inert towards all components of the reaction mixture. Suitable solvents include hydrocarbons such as benzene, toluene or xylene, or mixtures thereof; or nitriles such as acetonitrile or benzonitrile, or mixtures thereof. The unsaturated compound may, in some cases, serve as the solvent.

The preferred or optimal reaction temperature will vary depending on the particular catalyst and/or unsaturated compound employed in the reaction, and the desired reaction rate. In general, temperatures in the range of −25° to 200° C. are suitable, with 0° to 150° C. being preferred.

The pressure at which the invention process is carried out is not critical. Pressures in the range of about 0.05 to 10 atmospheres are preferred for economic reasons, although pressures of about 100 atmospheres or higher may be employed.

Hydrogen cyanide may be added to the reaction mixture as vapor or liquid, or in a system utilizing a cyanohydrin as carrier. See, for example, U.S. Pat. No. 3,655,723 which is incorporated herein by reference.

The present invention process is carried out in the presence of a promoter comprised of one or more Lewis acids which influence the activity and selectivity of the catalyst system. The promoter may be an inorganic or organometallic compound wherein the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Suitable promoters are further described in U.S. Pat. Nos. 3,496,217; 3,496,218; 4,774,353. These include metal salts such as $ZnCl_2$, $CoI_2$ and $SnCl_2$, and organometallic compounds such as $RAlCl_2$, $R_3SnO_3SCF_3$ and $R_3B$, where R is an alkyl or aryl group. U.S. Pat. No. 4,874,884 describes synergistic combinations of promoters for increasing the activity of the catalyst system. Preferred promoters are $CdCl_2$, $ZnCl_2$, $B(C_6H_5)_3$ and $(C_6H_5)SnX$, where X is $CF_3SO_3$, $CH_3C_6H_5SO_3$ or $(C_6H_5)_3BCN$. $ZnCl_2$ is most preferred. The molar ratio of promoter to nickel may be in the range of about 1:16 to 50:1, preferably about 1:10 to 10:1.

EXAMPLES

The following nonlimiting embodiments further illustrate and enable the process and catalyst precursor compositions of the invention.

General Procedure for HCN Reactions

Hydrocyanation reactions were carried out using the following procedure unless otherwise noted. The mixtures were heated in a thermostatically controlled oil bath. HCN was delivered to the reaction vessel as an $HCN/N_2$ gas mixture by bubbling dry nitrogen gas through liquid HCN at 0° C. (maintained in an ice bath); this provided a vapor stream containing about 35% by volume of HCN. The rate of nitrogen gas flow determined the rate of HCN delivery. Samples were analyzed by gas chromatography (GC) employing a DB23 column.

Examples 1, 2, 7, 10, 13 and 16 illustrate preparation of ligands (Ligand A–E) of the invention. Examples 3–6, 8, 9, 11, 12, 14, 15, 17 and 18 illustrate the hydrocyanation process of the invention wherein the unsaturated compound was 3-pentenenitrile (3-PN) and the nickel source was $Ni(COD)_2$. Example 19 illustrates hydrocyanation of 3-PN employing a conventional ligand, p-tritolylphosphite.

Example 1

Synthesis of Ligand A

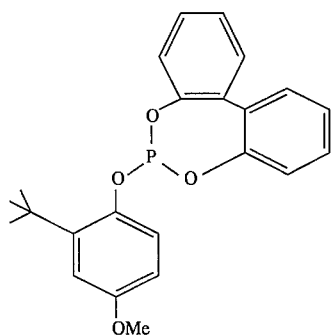

To 1.394 g of 1,1'-biphenyl-2,2'-diyl phosphorochloridite in 5 ml of tetrahydrofuran (THF) at −78° C. was added a 20 ml THF solution containing 0.563 g of triethylamine and 1.002 g of 2-t-butyl-4-methoxyphenol. The mixture was warmed to room temperature, stirred overnight, and then filtered through celite and washed with THF. Solvent was removed by rotary evaporation. The product obtained was 2.288 g of the desired Ligand A, {1-(1,1'-biphenyl-2,2'-diyl phosphite)-2-t-butyl-4-methoxyphenyl}, as a tan oil. $^{31}P$ {1H} nmr (121.4 MHz, $C_6D_6$): 146.6 ppm

Example 2

Synthesis of Ligand A

Phosphorus trichloride (49 ml) and 2-t-butyl-4-methoxyphenol (54.06 g) were mixed and refluxed for 2.5 h to give a clear light yellow solution. Distillation yielded 71.659 g of the desired dichloridite; boiling point 143° C. (at 0.4 mm Hg). $^{31}P$ {1H} (121.4 MHz, $C_6D_6$): 185.98 ppm. $^1H$ (300 MHz, $C_6D_6$): 7.36 (d, J=8.8 Hz, 1H), 6.99 (d, J=3 Hz, 1H), 6.38 (dd, J=3.0, 8.8 Hz, 1H), 3.3 (s, 3H), 1.27 (s, 9H). The dichloridite (2.0 g) was dissolved in 40 ml of toluene. A toluene solution containing 1.32 g of 1,1'-biphenol and 2.2 g of triethylamine was added dropwise to the dichloridite solution, and the mixture was refluxed for 1 h. After cooling to room temperature, the mixture was filtered through celite and washed with toluene. Solvent was removed by rotary evaporation to give 3.059 g of Ligand I. $^{31}P$ {1H} (121.4 MHz, $C_6D_6$): same as Example 1. $^1H$ nmr (300 MHz, $C_6D_6$): 7.4 (d, 1H), 7.3–7.0 (m, 9H), 6.6 (dd, 1H), 3.6 (s,3H) and 1.65 (s, 9H). High resolution mass spectrum: Found m/e: 394.1319; calculated for $C_{23}H_{23}O_4P$: 394.1334.

Example 3

Hydrocyanation of 3-PN; Ligand A; ZnCl$_2$ Promoter

Ligand A (375 rag), prepared in Example 1, and Ni(COD)$_2$ (40 mg, containing 0.14 mmoles of Ni) were dissolved in 5 ml of THF (P:Ni g atom ratio, 6.8). The solvent was removed by evaporation under vacuum and 5 ml of 3-pentenenitrile (3-PN) and 10 mg of ZnCl$_2$ were added. To the mixture was added HCN at 12 cc/min of nitrogen at 50° C. After 2 h, GC analysis indicated the presence of 21.3 mole % adiponitrile (ADN), 2.8 mole % methyl glutaronitrile (MGN), and 0.6 mole % ethyl succinonitrile (ESN). Selectivity to ADN was 86.2%.

Example 4

Hydrocyanation of 3-PN; Ligand A; Ph$_3$SnOTf Promoter

Example 3 was repeated except that 422 mg of Ligand A and 15 mg of (C$_6$H$_5$)$_3$SnO$_3$SCF$_3$ (in place of ZnCl$_2$) were used (P:Ni ratio, 7.6). After 2 h, GC analysis indicated the presence of 7.2 mole % ADN, 1.5 mole % MGN, and 0.7 mole % ESN. Selectivity to ADN was 76.6%

Example 5

Hydrocyanation of 3-PN; Ligand A; ZnCl$_2$ Promoter

Example 3 was repeated except that 330 mg of Ligand A and 20 mg of ZnCl$_2$ were used (P:Ni ratio, 6.0), and hydrocyanation was carried out at 70° C. After 2 h, GC analysis indicated the presence of 60.8 mole % ADN, 8.6 mole % MGN, and 1.6 mole % ESN. Selectivity to ADN was 85.6%.

Example 6

Hydrocyanation of 3-PN; Ligand A; ZnCl$_2$ Promoter

Ni(COD)$_2$ (40 mg) and 330 mg of Ligand A were dissolved in 5 ml of THF and the solvent was removed by vacuum evaporation. 5 ml of 3-PN and 20 mg of ZnCl$_2$ were added and the mixture treated with HCN with a nitrogen flow rate of 12 cc/min of nitrogen at 50°–100° C. temperature ramp. The oil bath temperature was initially 50° C.; after 15 minutes, the temperature was raised to 60° C. The temperature was subsequently set at 70°, 80° and 100° C. after 15 minutes intervals. Fifteen minutes after setting the temperature at 100° C., GC analysis indicated 38.7% of ADN, 6.2% of MGN and 1.2% ESN. Selectivity to ADN was 83.9%.

Example 7

Synthesis of Ligand B

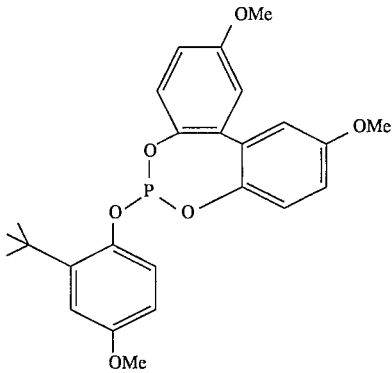

Part A: 2,2'-dihydroxy-5,5'-dimethyoxy-1,1'-biphenyl was prepared by the dealkylation of 2,2'-dihydroxy-3,3'-di-t-butyl-5,5'-dimethyoxy-1,1'-biphenyl using a procedure described by Tashiro, M.; Fukata, G., and Yamato, T.; Organic Preparations and Procedures Int., 8, 263 (1976). AlCl$_3$ (10 g) and 10 g of 2,2'-dihydroxy- 3,3'-di-t-butyl-5,5'-dimethoxy-1,1'-biphenyl were mixed in 125 ml of benzene and heated at 40° C. for 3 h. The mixture was cooled in ice and 125 ml of 10% HCl solution was added slowly. The organic layer was separated and washed with 3×125 ml of 10% NaOH. The basic solution was neutralized with concentrated HCl and extracted with 3×100 ml of ether. The ether layer was dried over Na$_2$SO$_4$. After filtering and removing the solvent by vacuum evaporation, the brown oil was washed with hexane and then the product crystallized from CH$_2$Cl$_2$/hexane. 2.202 g of 2,2'-dihydroxyl-5,5'-dimethoxy-1,1'-biphenyl was obtained as a white solid. $^1$H nmr (300 MHz, CD$_2$Cl$_2$): 6.9–6.8 (m, 6H), 5.71 (s, 2H), 3.78 (s, 6H).

Part B: To 2.0 g of a dichloridite, prepared by reacting PCl$_3$ with 2-t-butyl-4-methoxyphenol, in 40 ml of toluene was added 1.75 g of 2,2'-dihydroxyl-5,5'-dimethoxy-1,1'-biphenyl prepared in Part A, and 2.2 g of triethylamine in 20 ml of toluene. The mixture was refluxed for 1 h and then filtered through celite and washed with toluene. Removal of solvent by vacuum evaporation gave 3.475 g of white paste determined to be Ligand B, {1-(5,5'-dimethoxy-1,1'-biphenyl-2,2'-diyl phosphite)-2-t-butyl-4-methoxyphenyl}. $^{31}$P {$^1$H} (121.4 MHz, C$_6$D$_6$): 144.94; $^1$H nmr (300 MHz, C$_6$D$_6$): 7.5 (d, 1H), 7.1 (d, 2H; part of the doublet overlapped with residual benzene), 7.09 (d, 1H), 6.9 (d, 2H), 6.7 (dd, 2H), 6.5 (dd, 1H), 3.3 (s, 3H), 3.2 (s,6H), 1.4 (s, 9H) along with a small amount of toluene. High resolution mass spectrum: calculated for C$_{25}$H$_{27}$O$_6$P: 454. 1545; found: 454.1565.

Example 8

Hydrocyanation of 3-PN; Ligand B; ZnCl$_2$ Promoter

Ni(COD)$_2$ (40 mg) and 388 mg of Ligand B were dissolved in 5 ml of THF and the solvent was removed by vacuum evaporation. 5 ml of 3-PN and 20 mg of ZnCl$_2$ were added and the mixture treated with HCN with a nitrogen flow rate of 12 cc/min of nitrogen at 50° C. After 2 h, GC analysis indicated 44.4% of ADN, 4.6% of MGN and 1.1% ESN. Selectivity to ADN was 88.6%.

Example 9

Hydrocyanation of 3-PN; Ligand B; ZnCl$_2$ Promoter

Ni(COD)$_2$ (40 mg) and 388 mg of Ligand B were dissolved in 5 ml of THF and the solvent was removed by vacuum evaporation. 5 ml of 3-PN and 20 mg of ZnCl$_2$ were added and the mixture treated with HCN with a nitrogen flow rate of 12 cc/min of nitrogen at 50°–100° C. temperature ramp. The oil bath temperature was initially 50° C.; after 15 minutes, the temperature was set at 60° C. The temperature was subsequently set at 70°, 80° and 100° C. after 15 minute intervals. Fifteen minutes after setting the temperature at 100° C., GC analysis indicated 26.2% of ADN, 2.8% of MGN and 0.6% ESN. Selectivity to ADN was 88.5%.

Example 10

Synthesis of Ligand C

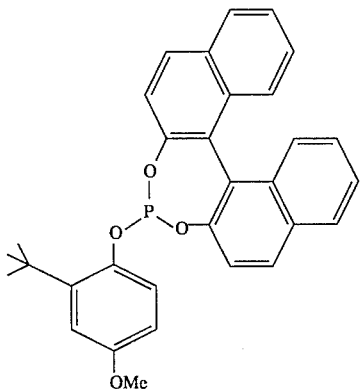

To 2.0 g of a dichloridite, prepared by reacting PCl$_3$ and 2-t-butyl-4-methoxyphenol in 40 ml of toluene, was added 2.04 g of 1,1'-bi-2-naphthol and 2.2 g of triethylamine in 20 ml of toluene. The mixture was refluxed for 1 h and then filtered through celite and washed with toluene. Removal of solvent by vacuum evaporation gave 3.844 g of white solid/clear liquid determined to be the desired Ligand C, {1-(1,1'-binaphthyl-2,2'-diyl phosphite)-2-t-butyl-4-methoxyphenyl}. $^{31}$P {$^1$H} (121.4 MHz, C$_6$D$_6$): 146.22; $^1$H nmr (300 MHz, C$_6$D$_6$): 7.6–7.4 (m, 9H), 7.0–6.8 (m, 4H), 6.5 (dd, 1H), 3.3 (s, 3H), 1.3 (s,9H) along with a small amount of toluene. High resolution mass spectrum calculated for C$_{31}$H$_{27}$O$_4$P: 494.1647; Found: 494.1660.

Example 11

Hydrocyanation of 3-PN; Ligand C; ZnCl$_2$ Promoter

Ni(COD)$_2$ (40 mg) and 422 mg of Ligand C were dissolved in 5 ml of THF and the solvent was removed by vacuum evaporation. 5 ml of 3-PN and 20 mg of ZnCl$_2$ were added and the mixture treated with HCN with a nitrogen flow rate of 12 cc/min of nitrogen at 50°–100° C. temperature ramp. The oil bath temperature was initially 50° C.; after 15 minutes, the temperature was set at 60° C. The temperature was set at 70°, 80° and 100° C. after 15 minute intervals. Fifteen minutes after setting the temperature at 100° C., GC analysis indicated 30.0% of ADN, 5.0% of MGN and 0.9% ESN. Selectivity to ADN was 83.6%.

Example 12

Hydrocyanation of 3-PN; Ligand C; ZnCl$_2$ Promoter

Ni(COD)$_2$ (40 mg) and 420 mg of the Ligand C were dissolved in 5 ml of THF and the solvent was removed by vacuum evaporation. P:Ni ratio of 6:1 with 0.14 mmoles of Ni. 5 ml of 3-PN and 20 mg of ZnCl$_2$ were added and the mixture treated with HCN with a nitrogen flow rate of 12 cc/min of nitrogen at 70° C. for 2 h. GC analysis indicated 41.7% of ADN, 7.9% of MGN and 1.3% ESN. Selectivity to ADN was 81.8%.

Example 13

Synthesis of Ligand D

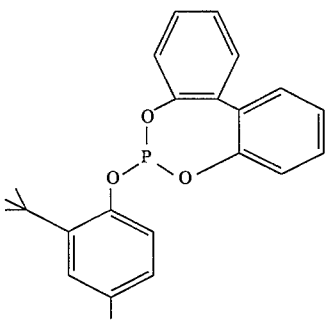

To 2.0 g of 1,1'-biphenyl-2,2'-diyl phosphorochloridite in 20 ml of toluene at room temperature was added 2.43 g of triethylamine and 1.31 g of 2-t-butyl-4-methylphenol in 20 ml of toluene. The mixture was stirred overnight. The mixture was filtered through celite, washed with 20 ml of toluene and solvent removed by rotary evaporation. Thus obtained was 3.015 g of the desired Ligand E, {1-(1,1'-biphenyl-2,2'-diyl phosphite)-2-t-butyl-4-methylphenyl} as a colorless liquid. $^{31}$P {$^1$H} nmr (121.4 MHz, C$_6$D$_6$): 146.4 ppm. $^1$H nmr (300 MHz, C$_6$D$_6$): 7.4 (d, 1H), 7.0–6.8 (m, 9H), 6.8 (dd, 1H), 2.1 (s, 3H), 1.4 (s, 9H) along with a little toluene. High resolution mass spectrum: calculated for C$_{23}$H$_{23}$O$_3$P: 378.1385; found: 378.1382.

Example 14

Hydrocyanation of 3-PN; Ligand D; ZnCl$_2$ Promoter

Ni(COD)$_2$ (40 mg) and 319 mg of the Ligand D were dissolved in 5 ml of THF and the solvent was removed by vacuum evaporation. 5 ml of 3-PN and 20 mg of ZnCl$_2$ were added and the mixture treated with HCN with a nitrogen flow rate of 12 cc/min of nitrogen at 50°–100° C. temperature ramp. The oil bath temperature was initially 50° C.; after 15 minutes, the temperature was set at 60° C. The temperature was set at 70°, 80° and 100° C. after 15 minute intervals. Fifteen minutes after setting the temperature at 100° C., GC analysis indicated 44.6% of ADN, 8.4% of MGN and 1.6% ESN. Selectivity to ADN was 81.7%

Example 15

Hydrocyanation of 3-PN; Ligand D; ZnCl$_2$ Promoter

Ni(COD)$_2$ (40 mg) and 370 mg of the Ligand D were dissolved in 5 ml of THF and the solvent was removed by vacuum evaporation (P: Ni ratio, 7:1; 0.14 mmoles of Ni). 5 ml of 3-PN and 20 mg of ZnCl$_2$ were added and the mixture treated with HCN with a nitrogen flow rate of 12 cc/min of nitrogen at 70° C. for 2 hours. GC analysis indicated 47.0% of ADN, 7.4% of MGN and 1.3% ESN. Selectivity to ADN was 84.4%.

Example 16

Synthesis of Ligand E

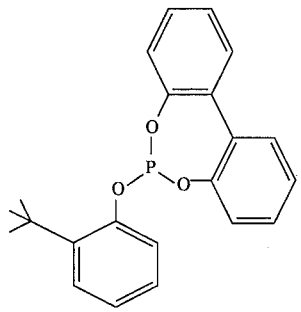

Part A: To 1.354 g of a dichloridite, prepared by reacting $PCl_3$ with 2-t-butylphenol, in 5 ml of THF was added 1.004 g of 2,2'-biphenol and 1.091 g of triethylamine in 10 ml of THF at −78° C. The mixture was stirred overnight and then filtered through celite and washed with THF. Removal of solvent by vacuum evaporation gave a colorless liquid determined to be the desired Ligand D, {1-(1,1'-biphenyl-2,2'-diyl phosphite)-2-t-butylphenyl}. $^{31}P$ {$^1H$} (121.4 MHz, $C_6D_6$): 146.43; $^1H$ nmr (300 MHz, $C_6D_6$): singlet at 1.3 ppm along with aromatic resonances.

Part B: To 2.0 g of 1,1'-biphenyl-2,2'-diyl phosphorochloridite in 20 ml of toluene at room temperature was added 1.0 g of triethylamine and 1.2 g of 2-t-butylphenol. The mixture was stirred overnight. The mixture was filtered through celite, washed with toluene and solvent removed by rotary evaporation. Thus obtained was 3.198 g of the desired Ligand E as a light tan liquid.

Example 17

Hydrocyanation of 3-PN; Ligand E; $ZnCl_2$ Promoter $Ni(COD)_2$ (40 mg) and 366 mg of Ligand E were dissolved in 5 ml of THF and the solvent was removed by vacuum evaporation. 5 ml of 3-PN and 10 mg of $ZnCl_2$ were added and the mixture treated with HCN with a nitrogen flow rate of 12 cc/min of nitrogen at 50° C. After 2 hrs, GC analysis indicated 7.2% of ADN, 1.1% of MGN and 0.2% ESN. Selectivity to ADN was 84.7%

Example 18

Hydrocyanation of 3-PN; Ligand E; $ZnCl_2$ Promoter $Ni(COD)_2$ (40 mg) and 306 mg of Ligand E were dissolved in 5 ml of THF and the solvent was removed by vacuum evaporation. 5 ml of 3-PN and 20 mg of $ZnCl_2$ were added and the mixture treated with HCN with a nitrogen flow rate of 12 cc/min of nitrogen at 50°–100° C. temperature ramp. The oil bath temperature was initially 50° C.; after 15 minutes, the temperature was set at 60° C. The temperature was set at 70°, 80° and 100° C. after 15 minute intervals. Fifteen minutes after setting the temperature controller to 100° C., GC analysis indicated 6.5% of ADN, 1.2% of MGN and 0.3% ESN. Selectivity to ADN was 81.25%.

Example 19

Comparative Example

Hydrocyanation of 3-PN; p-Tritolylphosphite; $ZnCl_2$ Promoter

To 205 mg of tetrakis(p-tolylphosphite)nickel, 99 mg of p-tritolylphosphite (P:Ni ratio of 6; 0.14 mmoles of Ni) and 20 mg of $ZnCl_2$ were added 5 ml of 3-PN. The mixture was treated with HCN under the same conditions as in Example 5. After 2 h, GC analysis showed the presence of 27.6% ADN, 6.1% MGN and 0.9% ESN. Selectivity to ADN was 80.0%.

I claim:

1. A process for hydrocyanation comprising reacting an acylic aliphatic monoolefin, said monoolefin being unconjugated or conjugated to an ester group, with a source of hydrogen cyanide in the presence of a catalyst precursor composition comprising zero-valent nickel and a monodentate phosphite ligand of Formula I,

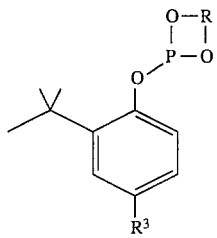

wherein:

R is

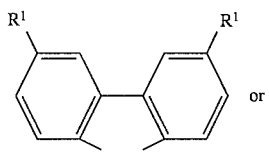

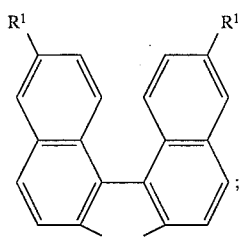

each $R^1$, independently, is H, $C_{1-8}$ alkyl or $OR^2$;

$R^2$, independently, is $C_{1-8}$ alkyl; and $R^3$ is H, $C_{1-8}$ alkyl or $OR^2$;

and wherein said reaction is carried out in the presence of a Lewis acid promoter, to produce a terminal organonitrile.

2. The process of claim 1 wherein the acyclic aliphatic monoolefin is a compound of the formula

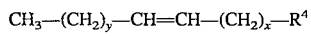

wherein:

$R^4$ is H, CN, $CO_2R^5$ or $C_z(F_{2z+1})$;

x is 0 or 1–5;

y is 0 or 1–5;

$R^5$ is $C_{1-8}$ alkyl; and z is 1–8;

with the proviso that, when $R^4$ is CN, x is not zero;

and the terminal organonitrile product is a compound of the formula $$NC-(CH_2)_{x+y+3}-R^4 \quad (IV)$$

wherein the symbols are as defined above.

3. The process of claim 1 wherein the acyclic aliphatic monoolefin is a compound of the formula $$CH_2=CH-(CH_2)_x-R^4 \quad (III)$$

wherein:

$R^4$ is H, CN, $CO_2R^5$ or $C_z(F_{2z+1})$;

x is 0 or 1–5;

$R^5$ is $C_{1-8}$ alkyl; and z is 1–8;

with the proviso that, when $R^4$ is CN, x is not zero;

and the terminal organonitrile product is a compound of the formula $$NC-(CH_2)_{x+2}-R^4 \quad (V)$$

wherein the symbols are as defined above.

4. The process of claim 1 wherein R is

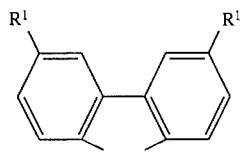

and each $R^1$, independently, is H, $C_{1-8}$ alkyl or $OR^2$ where $R^2$ is $C_{1-8}$ alkyl.

5. The process of claim 4 wherein each $R^1$ is H.

6. The process of claim 1 wherein $R^3$ is $OR^2$ wherein $R^2$ is $C_{1-4}$ alkyl.

7. The process of claim 6 wherein $R^2$ is methyl.

8. The process of claim 1 wherein the acylic aliphatic monoolefin is 3-pentenenitrile or 4-pentenenitrile.

9. The process of claim 1 wherein the terminal organonitrile product is adiponitrile.

10. The process of claim 1 wherein the Lewis acid promoter is an inorganic or organometallic compound wherein the cation is selected from the group consisting of the elements of atomic number 5, 13, 21–30, 39–42, 48–50 and 75.

11. The process of claim 10 wherein the Lewis acid promoter is $ZnCl_2$.

12. The process of claim 1 wherein the reaction temperature is in the range of about 0° to 150° C.

13. The process of claim 1 wherein $R^3$ is methyl and the monoolefin is 3-pentenenitrile.

14. A catalyst precursor composition comprising zerovalent nickel or a source thereof, and a monodentate phosphite ligand of Formula I

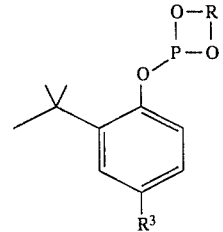

wherein:

R is

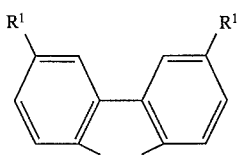

each $R^1$, independently, is H, $C_{1-8}$ alkyl or $OR^2$;

$R^2$ is $C_{1-8}$ alkyl;

$R^3$ is H, $C_{1-8}$ alkyl or $OR^2$;

and wherein the g atom ratio P:Ni is in the range of about 1:1 to 10:1.

15. The composition of claim 14 wherein $R^3$ is $OR^2$ and $R^2$ is methyl.

16. The composition of claim 14 wherein R is

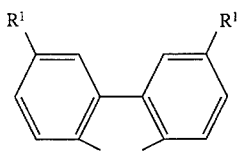

and each $R^1$, independently, is H, $C_{1-8}$ alkyl or $OR^2$ where $R^2$ is methyl.

17. The composition of claim 16 wherein each $R^1$ is H.

18. The composition of claim 14 wherein the ligand is selected from the group

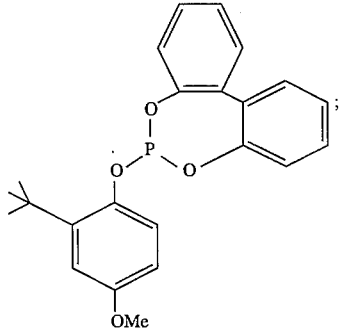

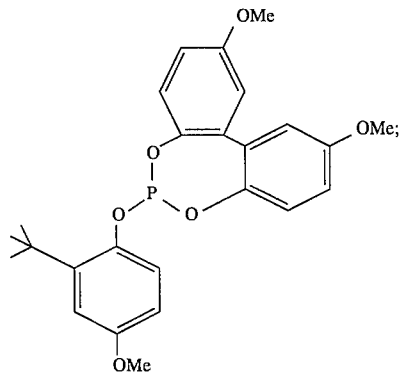

15
-continued
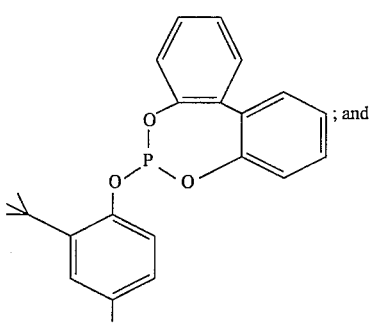
; and
16
-continued
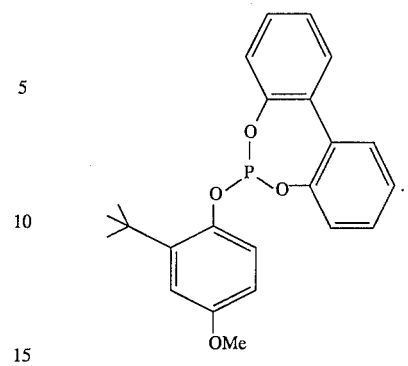
.
* * * * *